United States Patent [19]
Griffon

[11] 3,975,553
[45] Aug. 17, 1976

[54] DEPROTEINATION OF YEAST CELLS

[76] Inventor: Henri Griffon, 2 Place Mazas, 75012 Paris, France

[22] Filed: Sept. 13, 1974

[21] Appl. No.: 505,844

Related U.S. Application Data

[63] Continuation-in-part of Ser. No. 308,606, Nov. 22, 1972, abandoned, which is a continuation-in-part of Ser. No. 71,371, Sept. 11, 1970, abandoned, which is a continuation of Ser. No. 810,852, March 26, 1969, abandoned, which is a continuation of Ser. No. 532,107, March 6, 1966, abandoned.

[30] Foreign Application Priority Data

Mar. 8, 1965 France .................. 65.8314

[52] U.S. Cl. .................. 426/656; 195/74; 424/115; 426/40; 426/648; 426/804
[51] Int. Cl.² .................. A23L 1/28; C12C 11/26
[58] Field of Search ............. 426/60, 148, 204, 212, 426/364, 431, 506, 656, 804, 648; 195/57, 58, 60, 74, 97; 424/115, 123

[56] References Cited
UNITED STATES PATENTS

| | | | |
|---|---|---|---|
| 1,012,147 | 12/1911 | Nolf | 426/312 |
| 2,904,439 | 9/1959 | Cooper et al. | 426/60 |
| 3,051,576 | 8/1962 | Lendvai | 426/60 X |
| 3,378,377 | 4/1968 | Griffon et al. | 426/204 X |

FOREIGN PATENTS OR APPLICATIONS

| | | |
|---|---|---|
| 596,847 | 1/1948 | United Kingdom |

*Primary Examiner*—David M. Naff
*Attorney, Agent, or Firm*—Darby & Darby

[57] ABSTRACT

A deproteinated yeast cell membrane product is produced by autolysis of fresh compressed yeast containing about 70 to 71% moisture under anaerobic conditions to produce a pasty yeast mixture containing soluble material and deproteinated yeast cell membranes, and separating the yeast cell membranes from the mixture. Compressed yeast is the sole substance present during autolysis except for an inert gas which may be in contact with the yeast. The yeast cell membrane product has dietetic and therapeutic properties.

7 Claims, No Drawings

DEPROTEINATION OF YEAST CELLS

CROSS REFERENCE TO RELATED APPLICATIONS

This application is a continuation-in-part of application Ser. No. 308,606 filed Nov. 22, 1972, which is a continuation-in-part of application Ser. No. 71,371 filed Sept. 11, 1970, which is a continuation of application Ser. No. 810,852 filed Mar. 26, 1969, which is a continuation of application Ser. No. 532,107 filed Mar. 6, 1966, all now abandoned.

This invention relates to an anaerobic process for treating yeast cells which is carried out in such a manner that a yeast comprising essentially deproteinated yeast cells is obtained. This cellular product can be incorporated into various types of food products, pharmaceutical and therapeutic compositions, useful for dietetic and therapeutic purposes.

Yeast consist of single-cell micro-organisms. When observed under the microscope, each cell is seen to be limited by an ellipsoidal envelope containing the protoplasm, the nucleus, and lipidic inclusions as well as vacuoles and spores depending on the stage of development and the nature of the medium in which the cells are present.

The protoplasm is essentially consists of a protein gel which is more or less joined to the included lipidic corpuscles by lipoprotein linkages. Because of the key importance attached to utilization of the fermentation properties of yeast, especially in the bread making industry and certain therapeutic applications which make use of live yeast, the question of the preservation of yeast in the live form presents a number of different problems. In fact, yeast stays fresh in a form suitable for industrial utilization (so-called compressed yeast having a water content of 71%) only up to a maximum period of a few weeks, provided that it is kept in a suitably cooled medium. When left unattended, the yeast suffers degradation and undergoes modifications which result in a rapid transformation. For example, in the case of compressed yeast which has been kept in a closed vessel so that the yeast does not undergo evaporation there remains a viscous mass having an unpleasant odor which is manifestly unfit for almost all purposes and in particular for making bread. It has been observed under the microscope that, in this mass, the yeast cells remain apparently intact. However, closer study reveals that the cellular content has more or less completely escaped through an aperture in the cell which, in the majority of cases, is located at the extremity of a large diameter of the cell which has formed at the place at which the cell has separated from the mother cell, since this location constitutes a cicatricial zone of least resistance. From the morphological point of view, the cell remains apparently intact and retains therein in particular the refractive lipidic inclusions.

It appears from these observations that an autolytic process takes place in an aseptic medium and is in fact, the first stage of putrefactive evolution in the yeast, the yeast cell being thereby deprived of its protein protoplasmic gel.

In accordance with the present invention which applies preferably to yeasts of the genus saccharomyces cerevisiae but also to any class of yeast which is produced industrially and which is provided in the form of fresh compressed yeast, the process of autolysis is initiated and is continued under maintenance of well-defined anaerobic conditions so as to obtain in a regular and reliable manner a yeast product the cells of which are substantially devoid of the protein fraction.

In accordance with the invention it has now further been discovered that the yeast cells which are thusly deproteinated have outstanding and entirely unexpected properties both for therapeutic and dietetic purposes.

In accordance with the invention, extensive investigation has been carried out in order to determine the conditions under which deproteinated yeast cells could be obtained comprising a well-defined product having properties which would make them most suitable and desirable for these applications.

The starting materials for use in the instant invention are live compressed yeast containing 70–71% moisture, such product being readily available in commerce. The use of yeasts having a higher water content is also possible as starting material if the industrial application permits such a possibility.

Preferably saccharomyces cerevisiae (sometimes called beer yeast) is used as the starting material of this invention. The yeast must be fresh (i.e., made up of living cells) and is desirably in the form referred to as compressed yeast which is characterized by a water content of at least approximately about 70%. Most of the commercially produced fresh yeast materials used as the preferred starting ingredients of the invention contain 71% by weight of water and 29% by weight of (dry) yeast cells. The starting product therefore contains at least 29% (by weight) of dry yeast cells. Fresh, compressed yeast of the genus saccharomyces cerevisiae generally contains from about 10 to about 11 billion yeast cells per gram. Insofar as it is possible to determine, all of the yeast cells are alive in the compressed form. THe morphology of the cells is that of an ellipsoid having a diameter of approximately 6 to 8 microns and a length of between about 8 and 10 microns.

Generally speaking there are two methods for producing the yeast product of the present invention. Both procedures are carried out in conjunction with conventional equipment currently employed in the food and pharmaceutical industries. In the first process, autolysis of compressed yeast is carried out in a sealed container or reaction vessel which may generally be described as an autoclave of the type in which steam does not enter the reaction chamber but rather is introduced into a chamber surrounding and isolated from the reaction vessel.

In the second procedure which may be carried out in a shorter time period, the autolyzed yeast product is concentrated by evaporation of water under reduced pressure and in the presence of an inert (non-oxidative) gas and the product then collected.

In both of the above procedures the only material utilized is compressed yeast, and no further chemical substance of any significance to the deproteinization reaction is employed. The first process does not require the addition of anything other than compressed fresh yeast at any stage of the method which is carried out under anaerobic conditions. In the second process an inert gas is swept through the reaction vessel during the concentration phase. It will be appreciated that the process may be practiced with any inert (non-oxidizing) gas since the gas has no effect and plays no part in the autolysis reaction. The inert gas is utilized to form a non-oxidizing internal atmosphere in order to avoid the phenomena of oxidation during the deproteinizing operations. This, in turn, necessitates application of heat without allowing the thermal level to exceed 55°C. But in any event, the nitrogen (Helium, Neon, Argon, etc.) or other inert gas does not play any part either in autolysis or in the recovery of deproteinized yeast.

Briefly summarized, the first method of producing the deproteinized yeast product of the present invention comprises allowing the compressed yeast to stand at 55°C in a closed vessel under anaerobic conditions. After a few hours, the yeast liquefies and autolysis phenomena appear. In order to ensure that the protein content of the cells is expelled into the external medium to an appreciable extent, the autolysis is allowed to continue for at least several days. The course of the process can be followed on the one hand by inspection of samples of the autolysis mass under the microscope and on the other hand by determining the total nitrogen content of the clear aqueous phase following its separation from the residual (insoluble) cell membranes.

Referring in greater detail to the first process, an important aspect of this procedure involves making sure that the autolysis reaction (during which substantially more than half of the yeast cell's protein content is expelled from within the cell membrane) is carried out under anaerobic conditions. This is accomplished by filling the reaction vessel or container with the fresh compressed yeast product to capacity. It will be understood that after the reaction vessel is sealed shut, it is airtight and the contents are cut-off from any communication with the atmosphere. The small amount of residual air remaining within the reaction vessel after it has been filled and sealed are quickly consumed by the fresh yeast and converted to carbon dioxide. Thus, practically speaking, there will be no oxygen, air or any other oxidizable gas available to enable an oxidation reaction to proceed within the sealed chamber after a short period of time. The exact time required for the yeast to consume the oxygen content in the atmospheric air remaining in the sealed container will vary depending upon the degree of space remaining after filling the vessel to capacity, however in most instances there will be insufficient oxygen present to enable an oxidation reaction to occur after the container has been sealed for two or three hours.

The reaction vessel or container which is utilized in the first process may be generally described as an autoclave in that it comprises a pot, kettle or reaction chamber which may be sealed by means of a hinged cover or lid having a clamp-down or screw-type fastening arrangement. The reaction vessel containing the starting materials is surrounded by another chamber into which steam or hot water may be introduced for purposes of heating or it may be heated using any other suitable controlled heating means, i.e., burners, hot water bath, hot plate, etc. A preferred apparatus which is commonly employed in food and pharmaceutical laboratories includes an illuminated window or port in the side wall to permit observation of the contents while the reaction is in progress as well as a spigot or port controlled by a faucet for purpose of withdrawing samples of the reaction chamber contents in the course of treatment without admitting air into the reaction vessel. This is usually accomplished by means of a tube running from the spigot and below the surface of the compressed yeast material. Generally, the construction of the vessel also includes a thermometer for purposes of measuring the temperature of its contents.

After the reaction vessel or container has been loaded, the lid is closed and clamped shut thereby sealing the interior of the vessel from the external environment. Heat, preferably in the form of steam or other heated fluid is then introduced into the outer jacket of the vessel and regulated to maintain the temperature of the contents at about 55°C. It is important, however, that the temperature of the contents is not allowed to exceed 55°. In the preferred embodiment of the invention a yeast comprising 71% (by weight water) and 29% (by weight) of dry yeast cells is employed as the starting material. Thus, the contents of the reaction vessel are substantially liquid in nature. The interior pressure of the vessel at no time exceeds very low levels because of the relatively low temperature at which the autolysis is carried out. Since there is no need to introduce into the reaction vessel any other substance besides the yeast, the vessel does not require tubes, funnels or any other device or apparatus which would permit the introduction of a foreign substance of any nature. Optionally, the container may be equipped with an internal agitator or propeller which may be utilized to stir the materials during the reaction thereby accelerating the autolysis phenomena somewhat.

The length of time the yeast is allowed to remain at 55°C is principally a function of the quantity of material being treated, however, the minimum time period is generally not less than approximately two days and the maximum time period about 5 days.

Within three or four hours after the contents of the vessel have reached 55°C, it can be observed that the contents begin to darken and turn brown. This indicates the commencement of the autolytic process in which the yeast cells progressively expel their protoplasmic contents through an aperture which appears in the cell membrane. Anatomically, the aperture appears in that area of the cell membrane where the cell had initially separated from the mother cell. The location of the aperture is generally at a pole of the cell or near a pole.

The 55°C temperature is maintained until substantially more than 50% of the naturally present protein gel of the yeast cells has been expelled from the interior of all of the cells being treated. There are several techniques which may be employed to determine when the appropriate point has been reached and heating should be stopped. The preferred techniques involve either microscopic examination of yeast cells treated with a 1% solution of methylene blue, or ascertaining the extent of autolysis or deproteinization by assayinhg aliquots of material drawn from the reaction vessel and determining the total amount of nitrogen present in the watery lipid stage which can be separated from the residual cellular membranes. Preferably the microscopic examination technique is employed for controlling autolysis in both processes.

According to this technique, small samples of yeast cells are drawn off from the reaction product being treated. The samples are rinsed with a 1% methylene blue solution and then observed under a microscope at a magnification of about 400X. The protoplasm is living yeast cells (due to the hydrolytic enzymes contained therein) reduces the methylene blue to a leuco derivative which has a whitish color under the microscope. In dead yeast cells, the hydrolytic enzyme has been destroyed and a strong bond is formed between the methylene blue and the proteinaceous protoplasm of the cell causing the cell to appear bluish under microscopic examination. In those cells where the protoplasmic content has been expelled, the cellular membrane which remains is neither dyed blue nor is it dyeable. Thus, one can find simultaneously in the same mass of treated yeast, cells in different stages of dying. The percentage of cells which has been autolyzed and therefore deproteinized can easily be determined by inspecting cells under the microscope with the use of a conventional cell counting chamber such as a hemacytometer. When the percentage of cells that has been autolyzed reaches 100% (i.e., microscopic examination of samples taken from the reaction vessel and treated with methylene blue no longer shows any blue dye on the cell walls, which appear undyed or without color, and shows only the remaining active lipid inclusions within the shell formed by the cell walls) autolysis has been completed and heating is stopped. The well-known Kjeldahl assay technique can then be employed, if desired, to ascertain the chemical composition of the cellular product.

In most instances, the autolysis reaction will be completed at the end of about three days of treatment at 55°C.

When the process of protein expulsion has been completed, the residual cell membranes (which form an insoluble phase coexisting with the watery liquid phase containing the expelled protein material) are separated from the water liquid phase by suitable and conventional means and preferably by centrifugation in a high speed centrifuge. The watery liquid stage is then discarded and the remaining cell membranes washed with water during centrifugation. The deproteinated yeast cells thereby obtained are in the form of a pasty product having a viscous or creamy consistency, the water content of which can amount to as much as 88 or 90% while still retaining a creamy consistency. As compared to the starting compressed yeast cells, the product of the invention contains less than half the amount of protein as determined by Kjeldahl assay. It is also possible to dehydrate the creamy yeast suspension by heating and thereby to obtain deproteinized yeast in the form of an impalpable dry powder.

The second method is more rapidly carried out than the first and represents a more preferred method. As in the case of the first method, the second method involves only biological processing without the action of any chemical and in particular any acid or basic substance. In this case the compressed yeast is also maintained for a period of a few hours in a closed vessel at a temperature of about 55°C until liquefaction and the commencement of the autolysis process has occurred.

In practicing the second method of the invention a reaction vessel similar to that employed in the first process is utilized. However, the vessel is modified to include an inlet valve (usually positioned on the cover portion) through which a gas may be supplied to the interior. Also, an aspirator or vacuum pump is connected through an outlet valve on the cover of the reaction vessel to permit the interior pressure within the reaction chamber to be reduced. The exhaust port of the vacuum pump is connected to a conventional distillation apparatus of the type in which cold water is used to condense a gas. The outlet valve will only permit gas to pass from within the reaction vessel into the distillation column and not in the opposite direction. Thus the interior of the reaction vessel can be maintained in a sealed, airtight condition. The cold water distillation apparatus is of the conventional type well known in the art in which a supply of cold water is fed through a glass or copper tube in the shape of a coil or spiral. The gas or vapor to be distilled is carried in a glass tube or pipe in which the coil of tubing is positioned. The tube carrying the gas to be distilled is fitted with a collection spigot to drain any fluid which may condense in the tube as a result of the distillation procedure. In this manner it is possible to recycle the nitrogen gas back into the reaction vessel through the inlet valve.

The reaction vessel is loaded to maximum capacity (full) with fresh compressed yeast as in the first described process, sealed shut, and the contents heated to a temperature of about 55°C until commencement of the autolysis process can be confirmed either visually (by noting the appearance of liquefaction and a brownish coloration in the yeast), or through microscopic observation of samples drawn from the yeast material, or by analyzing the nitrogen content of fluid samples drawn from the vessel. In most instances the compressed yeast starting product must be heated for between two and four hours in the sealed vessel until the liquefaction and autolysis phenomena begins to occur.

Once the commencement of liquefaction has been confirmed, the yeast contents of the vessel are subjected to a concentration procedure involving evaporation under low pressure to reduce the proportion of residual water remaining with the yeast cells to preferably about 40–50% (by weight). This is accomplished by lowering the internal pressure of the reaction chamber containing the compressed yeast through the use of the aspiration apparatus or vacuum pump. It is important that the interior pressure be reduced to a level which is below atmospheric pressure in order to achieve the most efficient operation of the invention. Preferably, the internal pressure of the vessel is reduced to about 650 mm. of mercury. The contents of the vessel are maintained at about 55°C during this operation and are continuously stirred by means of the internal agitation apparatus. An inert (non-oxidative) gas is then introduced into the vessel through an inlet valve located on the cover, in order to facilitate the elimination of water vapor. The gas, usually anhydrous nitrogen, is continuously fed into the vessel to maintain the contents under a nitrogen atmosphere. Continued operation of the vacuum pump exhausts the nitrogen gas into the distillation apparatus while simultaneously maintaining the reduced pressure level and creating a current of gas through the reaction chamber containing the yeast material. It will be appreciated that water vapor within the reaction vessel will wet the nitrogen gas and thereafter be distilled from the gas in the condensation area of the cold water distillation apparatus.

The yeast mass is maintained (at 55°C) under the reduced pressure inert gas atmospheric conditions until a brownish mass having a pasty consistency is observed, this usually signaling complete autolysis of the starting product. Confirmation that the autolysis has been completed can be obtained using the microscopic and chemical evaluation (nitrogen assay) techniques previously discussed. In most instances it will require from one of two days from the time the initial heating was commenced to reach this point, however, the exact time will vary depending upon the quantity of material being treated, the extent to which it is agitated, and the method employed to heat the reaction vessel. The use of smaller quantities of the yeast material, more uniform heating (e.g., hot water or steam) and more vigorous agitation will generally reduce the time required to completely autolyze the contents of the reaction vessel.

After verifying that autolysis has been completed, the brownish pasty yeast product is removed from the reaction vessel, diluted with an approximately equal amount of water and heated to 55°C. The fluid containing the yeast product is then subjected to centrifugation (as for example in an Alfa-Laval continuous separation centrifuge) in order to separate the cellular membranes (i.e., deproteinized yeast cells) from the watery liquid fraction.

The separated cell membranes are then washed with water on a conventional continuous filtration apparatus and the wash water assayed using the well-known biuret or trichloroacetic acid procedures (to detect protein nitrogen) and the Kjeldahlization technique (to ascertain the presence of amino nitrogen). Washing is continued until the wash water is free of detectable protein nitrogen and amino nitrogen. The deproteinized yeast cells collected on the filter are obtained in the form of a creamy mass having a viscous consistency and consisting of approximately 88% to 90% water (by weight) and 12% to about 10% (by weight) of dry cellular materials.

Generally, beginning with about 50 kg of fresh compressed yeast according to the second method, about 9 to 10 kg of deproteinized yeast cells are obtained having the following characteristics:

Ionic reaction (in a watery atmosphere):

pH = 5.0

Raw residual proteins (total nitrogen × 6.25) = 20% to 23% reported in dry weight (instead of 45% to 50% in the initial dry yeast).

Lipids approximately 10 % to 13% reported in dry weight.

Mineral substances: reported in 1.3% dry weight.

Insoluble cellular residue: approximately 60% reported in dry weight.

It should be noted that only the protein contained in the protoplasmic gel of the yeast cell is expelled by the method of this invention, and that the protein constituents of the cell membrane remains relatively undisturbed.

There is obtained as a final product a product having a creamy consistency and a water content which can amount to 88–90%, depending on the method of separation, for instance filtration, employed. The creamy consistency of the product is in any event retained so that the product can be handled with ease and its physicochemical properites can be most advantageously employed in subsequent dietetic and pharmaceutical applications.

As in the case of the first procedure it is desirable to utilize reaction vessels equipped with internal agitators which speed up the autolysis reaction. Also, as in the operation of the first method described above, the deproteinization mechanism of the present method does not require the addition of any additive for deproteinization, and the inert gas employed in the latter technique plays no part in this reaction. Upon completion of autolysis and separation in both of the above described methods, the operator obtains an insoluble phase consisting of the deproteinized yeast cells and more specifically of the membranes or the cellular shells of the initial yeast. The shells appear to be substantially intact under microscopic examination, with the exception of an aperture through which protein gel or a portion thereof has escaped, and a liquid stage containing the amino acids derived from the autolysis of the protoplasmic protein gel. The liquid phase is easily separated from the insoluble phase by filtration or centrifugation. The insoluble phase represents the sought after deproteinized yeast product of the invention, while the soluble phase represents a nitrogenous yeast extract.

The new and novel yeast product which is obtained by the process of the invention has the following morphological and physicochemical characteristics. Examination under the microscope shows the substantially intact cell membranes of the yeast cells. In the large majority of cases, there can be observed an opening in the cell membrane through which the protein gel has escaped. However, the refractive lipidic corpuscles have been retained and can be observed within the wall structure of the cell membrane. A suspension of such cell membranes in water is possessed of dispersing properties with respect to a large number of substances and especially lipidic substances. This property can be utilized in connection with the manufacture of cosmetic and pharmaceutical bases.

The results (averages) of several analytical determinations carried out on samples having a moisture content of 89% are given hereunder:

| - Ion reaction | pH - 5.0 |
|---|---|
| - Dry residue | 13.0% |
| - Fat | 1.3% |
| - Residual raw proteins (total nitrogen × 6.25) | 3.0% |
| - Mineral substances (incineration residue) | 0.45% |
| - Non-nitrogenous extractive | 8.4% |

It is worthy of note that the residual protein content indicated which corresponds to 23% of dry material has been determined by measuring the total nitrogen content by the Kjeldahl method. Using this method it is not possible to discriminate between the nitrogen which may be derived from the intracellular protein residue or from proteins which can make up the cell membranes.

In any case, if it is considered that the non-deproteinated dry yeast contains approximately 9% total nitrogen content, which corresponds to approximately 50.9% protein, it will be conceded that the deproteination yield is appreciably higher than 50% in the sample referred to above. In fact, as a result of operations based on the discovery of a biological process and of quantitative extraction techniques, the yield above set out is very satisfactory. It should be pointed out in addition that, apart from the residual nitrogen which can correspond to the cell membranes, residual nitrogen cannot remain in the product in protein form because of the intensity of the hydrolysis processes which take place. Irrespective of the appreciation of the residual nitrogen content the process of the invention provides a product which can be considered as substantially completely depleted of proteins, with the result that said product effectively meets the definition of a deproteinized yeast.

Finally, the high content of non-nitrogenous extracted substances is to be noted. Included among these substances are the products of the degradation of the cellular constituents and membranes and in particular, of the gummy and mucilaginous colloidal products present in the cellular membrane mass.

The preservation of the novel product in accordance with the invention is ensured for a certain period of time at ordinary temperature by virtue of its acid reaction which prevents the proliferation of most bacterial species which would otherwise be able to contaminate said product.

In certain cases, however, it is possible to incorporate into the cellular membrane material certain antiseptic substances which will not interfere with the subsequent uses of this material.

The creamy consistency of the novel product of the invention can vary over a wide range as already can be made more or less thick by conventional concentration techniques.

The novel product in accordance with the invention can also be dehydrated more or less completely by any of the known methods as for instance nebulization, atomization, lyophilization, etc. One such method has been described by H. Griffon in French Pat. No. 1,323,626 of Feb. 27, 1962.

Depending on the method of dehydration employed, the novel product can be obtained directly or if necessary it can be reduced to more or less finely divided powders again using conventional techniques.

As a result of partial dehydration which can be effected, for example, by concentration under low pressure, a product can also be obtained in the form of a paste which has a more or less thick consistency.

In the Nolf U.S. Pat. 1,012,147 a cellular preparation is disclosed which essentially consists of destroyed cellular membranes (see the drawing forming a part of this disclosure). These are easily distinguished from the deproteinized yeast cells of the invention consisting essentially of the yeast cell membranes enclosing refractive lipidic corpuscles.

The products can also be distinguished chemically as can be seen from the following Table.

TABLE

|  | Deproteinized yeast (application | Nolf |
|---|---|---|
| Lipids | 10–12% | 4–5% (4 preparations) |
| Nitrogen total | 3.5–3.8% | 1.0% |
| Peroxides | absent | present |

Further chemical analysis showed the following:

|  | deproteinized yeast (application) | Nolf |
|---|---|---|
| Sterols (notably ergosterol) (lipids sterol-like) | Presence is very important amounting to about ⅔ of the lipids totalling about 7% | Scant traces |
| Invertase | 1g of the deproteinized yeast was emulsified in 50 ml of a 2% saccharose solution. After 1 hour at 37°C more than 50% of the saccharose was converted to invert sugar. | 1g of the product was treated as described. After about 1 hour no inversion of the saccharose was observed. |

The results of the study show that the products prepared by the process of the invention and according to Nolf U.S. No. 1,012,147 differ in kind morphologically, chemically and enzymatically.

The therapeutic activity of the deproteinated yeast as hereinabove defined has been evaluated in a number of different human skin conditions; the procedures utilized involving external application of the product. However, there should not be overlooked the activity of the products of the invention in connection with other medical conditions involving also internal administration as will be hereinafter set out.

A first series of experiments has served to demonstrate the substantially complete tolerance of the skin to the new medicament which is provided in accordance with the invention.

The medicament of the invention was applied to volunteers selected from the medical and other personnel of a hospital and also included voluntary patients, all being free of any skin condition.

The experiment consisted in the application twice daily of 2 to 5 cm$^3$ of the product over the entire surface of the inner face of the left forearm. Prolonged massaging of the product onto the skin resulted in practically complete absorption of the product by the epithelial layer and was carried out with each application of the product.

The experiment was also carried out in a group of subjects after first degreasing the skin with ether.

In addition, in six subjects the application of the product took place after first abrading the skin with very fine emery paper over an area of 3 cm$^2$.

In none of the cases was any secondary reaction observed, nor any redness irritation unpleasant sensation. The majority of patients reported that after penetration of the product, an increased suppleness of the skin and a feeling of coolness was observed. Repeated applications of the product did not give rise to any manifestation of an allergic nature which could be characterized as sensitization.

After having observed the soothing and softening action of the new medication on healthy skins, its therapeutic activity was evaluated in subjects afflicted with lesions such as burns, eczematour sores whether infected or not, varicous ulcers, gluteal scabs, psoriasis, etc.

The tolerance to the medicament of the invention was perfect in all of the cases studied. No pain was reported after application of 2 to 5 cm$^3$ of the product. No pain, irritation or secondary intolerance were observed even after daily application of the product for more than fifteen days. The foregoing treatment did not in any case result in any instance of infection where no infection was originally present or of an increase in infection originally present as is so frequently observed in these conditions. There was observed on the contrary a remarkable cicatrising action of the wounds and sores, ulcers, scabs, etc.

The application of the novel medicament to skin conditions of the above types results in a cleaning of the affected part, followed rapidly by granulation of the base and the appearance of very sharply defined zones of proliferation of the epithelial edges.

The time for complete healing or cicatrisation to take place following the application twice daily of approximately 5 mm$^3$ of cream in accordance with the invention naturally varies according to the patient treated and the severity of the lesion.

However, it may be concluded that the therapeutic action of the novel medication on the basis of deproteinized yeast is comparable with that of the best cicatrizants which are at present available.

The novel medication also has a remarkable therapeutic action on dermatological conditions such as, for example, seborrheic acne whether there is present a purulent condition or not.

By way of non-limitative example, there is noted the case of a young girl who had had eruptions of acne over a period of two years and who had reacted more or less to a number of different treatments prescribed both local or general, the condition having developed in successive outbreaks which left disfiguring scars each time.

Application of the novel medicament on the basis of deproteinated yeast to the affected skin of the said subject checked further outbreaks fairly rapidly. In two or three weeks no further outbreaks occurred and there was observed on the one hand substantially complete epithelization of the lesions without any visible scar formation, no further outbreaks even after several months had elapsed, i.e., in effect a total discontinuance of outbreaks.

These highly desirable results are obtained by the application either daily or twice daily of the novel medicament in accordance with the invention or of pharmaceutical compositions which essentially consist of the novel medicament and suitable amounts of various pharmaceutically acceptable excipients or vehicles as conventionally employed for the purpose of providing medicaments in different forms of applications adapted for external administration, such as for example, ointments, creams, lotions, powders.

In accordance with the invention it has now been found that the novel deproteinated yeast in accordance with the invention also has advantageous dietetic properties.

In this connection a series of experiments have been carried out for determining the effect of the deproteinized yeast on the growth process of animals and especially on the growth processes of chickens.

The experiments established that the deproteinized yeast of the invention does not contain any growth factor and, on the contrary, appeared to delay the growth process of the test animals.

The following table sets forth the results of the experiments performed on day-old chicks of the Wyandotte breed for egg production. A batch of 20 chicks was fed normally and constituted the control batch. One group of chicks were subjected to a special diet in which 20% of the feed consisted of the deproteinized yeast in accordance with the invention. Still another batch was fed a diet in which 50% of the feed consisted of the deproteinized yeast.

TABLE

Batches of 20 male chicks*   Hatched on May 28th

| Date | Number of days | Control batch | Powder: 20% | Powder:50% |
|---|---|---|---|---|
| May 29th | 0 | 45.0 | 45.0 | 45.0 |
| June 1st | 3 | 47.5 | 48.0 | 43.6 |
| June 5th | 7 | 63.5 | 63.5 | 52.5 |
| June 8th | 10 | 90.0 | 80.0 | 57.1 |
| June 17th | 19 | 157.5 | 129.0 | |
| June 24th | 26 | 262.5 | 246.0 | |
| July 2nd | 34 | 454.0 | 347.0 | |

Unitary weight of chicks

*Breed: Wyandotte chicks for egg production

It was found that, after eight days, the growth of the chicks which have been fed with the feed having a 20% deproteinized yeast content was significantly inhibited as compared to the growth of the chicks of the control batch. This delayed development became more marked as the experiment was continued.

In the case of chicks whose food supply consisted of the feed having a 50% content of deproteinized yeast, the experiment was not continued over a period of more than 8 days since it became manifestly apparent that the chicks were not receiving a sufficient quantity of nutritive elements to ensure even retarded growth.

It accordingly appeared that the deproteinized yeast could be introduced into dietary products as an active agent for combating and controlling obesity. To this end, the deproteinized yeast was employed in preparing formulations for evaluations as obesity control aids.

In the dietetic formulations, the novel product in accordance with the invention is advantageously employed in its dehydrated form. The dehydration is more or less complete depending on the process which has been followed.

The composition of the novel dietary product in accordance with the invention in its preferably completely anhydrous form is as follows:

| | |
|---|---|
| Moisture | 0.0 |
| Raw proteins | 22.5 |
| Fats | 10.6 |
| Non-nitrogenous extract (cell shells or membranes) | 63.6 |

The non-nitrogenous extracted substances which comprise in the main degraded cellular shells are not digestible, swell in the presence of water and thus perform the function of roughage. These substances also have mucilaginous properties which endow the resultant product with a favorable action in the intestinal tract.

The composition of the conventionally available dry yeast as compared with the deproteinized yeast in accordance with the invention is summarized in the following table:

| | Therapeutic calorific value | Water | Simple proteins | Lipids | Glucides |
|---|---|---|---|---|---|
| Dry food yeast | Max. 340 | 8 | 45 | 2 | 35 |
| Deproteinized yeast | Approx. 150 | 8 | 20 | 9 | 58.5 |

The above comparison is fairly arbitrary as the three basic components which are normally involved in the calculation of the calorific value are not completely assimilable, especially insofar as concerns deproteinized yeast.

In the table, the element which is indicated as a glucide is in fact a "non-nitrogenous extract" as represented morphologically by the cell membranes which have withstood the hydrolysis processes employed in the preparation of the product together with a small proportion of what can be considered as assimilable glucides.

The same applies in the case of the simple proteins. As explained above, the simple protein content is expressed by the calculation which starts from the total nitrogen content as determined analytically; however, in the case of deproteinized yeast a part of the total nitrogen is to be referred to the cell membranes and consequently to a non-assimilable fraction.

So far as the lipids are concerned, they are constituted by a substantial unsaponifiable sterol fraction the calorific value of which cannot be compared with that of the alimentary glycerides.

The results of the above is that the calorific values given in the table are approximate and only indicate an order of magnitude.

In spite of this approximate character, the conclusion can nevertheless be drawn that the calorific value of the deproteinized yeast as well as the simple protein content thereof are scarcely one-half that of the known dry yeast product.

The novel dietary product of the invention can be utilized for combating obesity and are to this end advantageously utilized in the form of novel dietetic compositions which have a weight-reducing action.

The amount of the product in accordance with the invention which is to be introduced into a dietetic composition will vary according to the intensity of the effect which it is desired that the end product should have. The amounts preferably range between a minimum of 10% to a maximum of 60% of the total composition, although this maximum can be exceeded without any major disadvantage.

The novel dietary product of the invention can be associated with all food products such as eggs, flour, sugar, starch, chocolate, milk and utilized as such in the preparation of biscuits, shortbread, tablets, pills, breakfast powders, puddings, dessert preparations and the like.

The following examples are given by way of non-limitative examples of the invention.

| Fruit Powder | |
|---|---|
| Deproteinized yeast | 50 pts. by wt. |
| Strawberry powder | 20 pts. by wt. |
| Icing sugar | 10 pts. by wt. |
| Powdered skimmed milk | 10 pts. by wt. |
| Chocolate Powder (Breakfast) | |
| Deproteinized yeast | 60 pts. by wt. |
| Powdered skimmed milk | 15 pts. by wt. |
| Chocolate | 25 pts. by wt. |
| Corn starch | 5 pts. by wt. |
| Sugar | 15 pts. by wt. |
| Dry Biscuit | |
| Deproteinized yeast | 60 pts. by wt. |
| Corn starch | 15 pts. by wt. |
| Skimmed milk | 10 pts. by wt. |
| Margarine | 5 pts. by wt. |
| Flavoring (as required) | 5 pts. by wt. |
| Chemical yeast | 2-5 pts. by wt. |

Broadly speaking, the deproteinized yeast can be used to systematically replace any or all of the flour which is conventionally introduced into the culinary preparations.

What is claimed is:

1. The process of making a deproteinized yeast cell membrane product which comprises filling to capacity a vessel solely with compressed yeast having a moisture content of about 70%, sealing the filled vessel so that the vessel is air-tight and the yeast therein is cut off from communication with atmospheric air, heating the yeast in the vessel to about 55°C and maintaining the yeast at about 55°C under anaerobic conditions until liquifaction and autolysis of the yeast has commenced as indicated by the yeast beginning to darken and turn brown, thereafter lowering the internal pressure of said sealed vessel to less than atmospheric pressure and introducing an inert gas into said vessel to create a current of inert gas through the vessel and maintain said anaerobic conditions, evaporating residual water from yeast in said vessel while continuously agitating said yeast in the presence of said current of inert gas under said lower pressure at about 55°C until the proportion of residual water in said yeast has been reduced to about 40% to 50%, maintaining the yeast under said reduced pressure, said current of inert gas, said anaerobic conditions and said temperature until autolysis is complete and substantially more than 50% of the naturally present protein gel of the yeast cells has been expelled from within the yeast cells to form a pasty yeast product mixture of a water soluble material and deproteinated yeast cell membranes, recovering the cell membranes from said mixture by centrifugation, and washing the cell membranes with water.

2. The process of claim 1, which comprises sweeping said inert gas through said closed vessel and into a condensation apparatus during said evaporation step.

3. The process of claim 2, which comprises inspecting samples of said yeast product withdrawn from said vessel during said evaporation step to determine when autolysis has been completed.

4. The process of claim 1, wherein said inert gas is nitrogen.

5. The process of claim 4, which includes drying said deproteinized yeast product at room temperature to form a powder.

6. The process of claim 1 which includes washing said cell membranes until the wash water is free of detectable protein nitrogen and amino nitrogen.

7. The product produced by the process of claim 1 consisting essentially of natural deproteinated yeast cell membranes, said cell membranes containing the refractive lipidic corpuscles of the natural yeast cells and substantially less than 50% of the protein gel present in natural yeast cells and the morphology of a majority of the membranes of said yeast cells being characterized by a polar aperture not present in natural yeast cells and having the following composition:

| | | |
|---|---|---|
| dry residue | 13.0 | % |
| fats | 1.3 | % |
| residual raw proteins | 3.0 | % |
| mineral substances | 0.43 | % |
| non-nitrogenous extractives | 8.4 | %. |

* * * * *